(12) United States Patent
Watanabe et al.

(10) Patent No.: US 7,428,527 B2
(45) Date of Patent: Sep. 23, 2008

(54) DATA DISTRIBUTION METHOD, DATA SEARCH METHOD, AND DATA SEARCH SYSTEM

(75) Inventors: Tsunehiko Watanabe, Tokyo (JP); Junji Yoshii, Tokyo (JP); Tadashi Mizunuma, Tokyo (JP); Yuichi Minesaki, Tokyo (JP); Fumitoshi Ogura, Tokyo (JP); Keisuke Yamamoto, Tokyo (JP); Tateo Nagai, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 395 days.

(21) Appl. No.: 10/720,178

(22) Filed: Nov. 25, 2003

(65) Prior Publication Data

US 2004/0139051 A1    Jul. 15, 2004

(30) Foreign Application Priority Data

Nov. 27, 2002    (JP) .............................. 2002-344452

(51) Int. Cl.
G06F 7/00 (2006.01)
G06F 12/00 (2006.01)
G01N 33/48 (2006.01)

(52) U.S. Cl. ..................... 707/3; 707/104.1; 707/200; 702/19

(58) Field of Classification Search ............... 707/1–10, 707/100–102, 104.1, 200–201; 715/501.1, 715/51, 205, 234; 709/219; 435/6, 7.1; 702/19
See application file for complete search history.

(56) References Cited

U.S. PATENT DOCUMENTS

| | | | | |
|---|---|---|---|---|
| 4,774,655 A | * | 9/1988 | Kollin et al. ................... 707/4 |
| 5,737,595 A | * | 4/1998 | Cohen et al. ................. 707/100 |
| 5,873,082 A | * | 2/1999 | Noguchi ........................ 707/3 |
| 5,978,804 A | * | 11/1999 | Dietzman .................... 707/10 |
| 6,453,245 B1 | * | 9/2002 | Rothberg et al. .............. 702/20 |
| 6,470,277 B1 | * | 10/2002 | Chin et al. .................... 702/19 |
| 6,654,755 B1 | * | 11/2003 | Vanska ....................... 707/100 |
| 6,745,179 B2 | * | 6/2004 | Laronge et al. ................ 707/3 |
| 6,927,779 B2 | * | 8/2005 | Mannion et al. ............. 345/594 |

(Continued)

FOREIGN PATENT DOCUMENTS

WO    WO 01/13105 A1    7/2000

OTHER PUBLICATIONS

Eckman et al., "The Merck Gene Index Browser: An Extensible Data Integration System for Gene Finding, Gene Characterization and EST Data Mining", Oxford University Press, (1998) vol. 14, No. 1, pp. 2-13.

(Continued)

Primary Examiner—Miranda Le
(74) Attorney, Agent, or Firm—Reed Smith LLP; Stanley P. Fisher, Esq.; Juan Carlos A. Marquez, Esq.

(57) ABSTRACT

Necessary information can be easily extracted from a plurality of databases 11 in which biological substance information is stored. Data is downloaded from the plurality of databases. From the downloaded data is extracted information indicating links between two databases, a detailed description of each data, and sequence data for homology search, which together constitute an index. The thus extracted index 15 is distributed to a user facility, where a user 18 conducts a search using the distributed index.

2 Claims, 21 Drawing Sheets

U.S. PATENT DOCUMENTS

| | | | |
|---|---|---|---|
| 6,928,368 B1* | 8/2005 | Bulla et al. | 702/19 |
| 6,931,396 B1* | 8/2005 | Topaloglou et al. | 707/4 |
| 6,941,317 B1* | 9/2005 | Chamberlin et al. | 707/102 |
| 7,133,780 B2* | 11/2006 | Siani-Rose et al. | 702/20 |
| 2002/0132258 A1* | 9/2002 | Okubo et al. | 435/6 |
| 2002/0168664 A1* | 11/2002 | Murray et al. | 435/6 |
| 2002/0194154 A1* | 12/2002 | Levy et al. | 707/1 |
| 2002/0194201 A1* | 12/2002 | Wilbanks et al. | 707/104.1 |
| 2003/0041053 A1* | 2/2003 | Roth | 707/3 |
| 2003/0100996 A1* | 5/2003 | Yang et al. | 702/19 |
| 2003/0100999 A1* | 5/2003 | Markowitz | 702/20 |
| 2004/0024535 A1* | 2/2004 | Lincoln et al. | 702/20 |

OTHER PUBLICATIONS

W. Fujibuchi et al., "DBGET/Link DB: An Integrated Database Retrieval System", GenomeNet, (1998), pp. 683-694.

"How to Use DBGET", Institute for Chemical Research, Kyoto University, (2002), pp. 1-4.

R. Apweiler et al., "Introduction to Molecular Biology Databases", European Bioinformatics Institute, (1999), pp. 1-26.

European Search Report dated Aug. 1, 2005.

Okubo, Koichi, "How to Use the GenomeNet Database", Japan: Kyoritsu Shuppan Co., Ltd. (Mitsuaki Nanjo), Nov. 15, 2002, 3$^{rd}$ edition, pp. 11-24 and pp. 32-35; 4$^{th}$ edition, pp. 3-47, in Japanese with partial English translation.

* cited by examiner

| KeyDB | ROUTE | TargetDB |
|-------|-------|----------|
| A | B | C |
| A | B, C | D |
| A | B, C | E |
| .... | .... | .... |
| | | |

| No. | Nucleotide(EST) | Hit Count | Swiss-PROT |
|---|---|---|---|
| 1 | Hs.75061 | 1 | P25054 |
| 2 | Hs.19438 | 1 | Q13315 |
| 3 | Hs.19465 | 1 | Q14514 |
| 4 | Hs.20058 | 1 | Q60241 |
| 5 | Hs.8074 | 1 | Q60242 |
| 6 | Hs.54089 | 1 | Q99728 |
| 7 | Hs.36820 | 1 | P54132 |

Key DB  Target DB

View Route

FIG.18

```
> Query001
      1  gaattcca....  ─────  ─────  ─────  ─────  ─────  ─────
     61  ─────  ─────  ─────  ─────  ─────  ─────  ─────
    121  ─────  ─────  ─────  ─────  ─────  ─────  ─────
    181  ─────  ─────  ─────  ─────  ─────  ─────  ─────
```

FIG.20

Sequences producing significant alignments:

| | Score(bits) | E value |
|---|---|---|
| EST\|BF570078\|602186096T1 NIH_HGC_45 Homo sapiens cDNA clone.... | 595 | e-168 |
| EST\|BQ917841\|AGENCOURT_8842358 Lupski_sciatic_nerve Hom... | 575 | e-162 |
| EST\|BQ774659\|UI-H-FHO-bcc-p-09-0-UI.s1 NCI_C GAP_FHO Ho... | 575 | e-162 |
| EST\|BQ773379\|UI-H-FEO-bby-c-13-0-UI.s1 NCI_C GAP_FEO Ho... | 575 | e-162 |
| EST\|BQ773190\|UI-H-FEO-bbv-j-22-0-UI.s2 NCI_C GAP_FEO Ho... | 575 | e-162 |
| EST\|BQ772786\|UI-H-FEO-bbu-i-13-0-UI.s2 NCI_C GAP_FEO Ho... | 575 | e-162 |
| EST\|BQ772734\|UI-H-FEO-bbr-m-04-0-UI.s1 NCI_C GAP_FEO Ho... | 575 | e-162 |
| EST\|BQ668365\|AGENCOURT_8303633 NIH_HGC_102 Homo s.... | 575 | e-162 |
| EST\|BQ581190\|ii05h01.y1 Human insulinoma Homo sapiens cDNA... | 575 | e-162 |
| EST\|BQ549102\|ik88f09.y1 Human insulinoma Homo sapiens cDNA... | 575 | e-162 |

>EST | BF570078 | 602186096T1 NIH_HGC_45 Homo sapiens cDNA clone IMAGE : 4310639 3' .
    Length = 1040

Score = 595 bits (300) , Expect = e-168
Identities = 300/300 (100%), Gaps = 1/298 (0%)
Strand = Plus / Plus Query: 1    tgaagct·········
            |||||||
Sbjct: 50   tgaagct·········

Query: 63   ·········

Sbjct: 109  ·········

Query: 123  ·········

Sbjct: 169  ·········

DATA DISTRIBUTION METHOD, DATA SEARCH METHOD, AND DATA SEARCH SYSTEM

BACKGROUND OF THE INVENTION

1. Technical Field

The present invention relates to a method of retrieving information from a plurality of databases in which information about biological substances, such as sequences of bases and proteins, are stored, by associating the databases with one another and thus clarifying the connections among them.

2. Background Art

Databases storing information about biological substances exist all over the world and are available to the public on the Web. Biology researchers can take advantage of those databases for their own studies (see Non-patent document 1). Open databases related to gene information and protein information have their own unique registration numbers (to be hereafter referred to as IDs), which are in many cases assigned to the genes and proteins stored in the databases. So far, when a researcher searches open databases for his own data to retrieve data from the databases, it has been necessary for him to relate his own data with the ID of the particular database using some kind of means. According to the most typical method for that purpose, a homology search is carried out between the base sequence or protein sequence the researcher possesses and the base sequence or protein sequence stored in the database, such that they can be associated with one another.

This can be carried out in two ways. One has the researcher search the open databases on the Web for his own data one-by-one. The other involves the researcher downloading the data of the databases on the Web into his own facility one-by-one and then searching the data, in order to avoid the chances of information leakage that could happen during a search via the Internet. FIG. 21 schematically shows a search system according to the prior art whereby the data is downloaded from databases on the Web. A user 218 downloads files 219 one by one from an open database 211 via the Internet 212 to a facility 217 of the user. The user 218 then carries out a search on the thus downloaded files 219.

(Non-patent document 1) Baxebanis, A. D: Nucl. Acids Res., 28:1-10, 2000, "Genetics Databases" (Bishop M. J. ed.), Academic Press, Cambridge, 1999.

SUMMARY OF THE INVENTION

It has been possible to search for information on the Web on a one-by-one basis because of the limited number of data items, typically in the range between one to 10, that had to be handled by the researcher at one time. However, the recent technological advances have allowed hundreds or even thousands of data items to be handled, making it extremely burdensome to search them one by one. The search conducted on a plurality of open databases has also resulted in the creation of unnecessary data, from which the researcher had to re-extract information of his interest. Furthermore, there are so many databases around the world that the researcher has to evaluate and decide on which databases are necessary for him. Some databases contain a plurality of biological species (such as humans, mice, and rice), and no systems have been available for retrieving data concerning a certain living species from various databases in a comprehensible manner. Nor have there been any systems for retrieving data according to the type of data (DNA, mRNA, EST).

In the case of downloading data from open databases one by one into the user's facility, this could take so much time if the amount of data to be downloaded is large that the line could be interrupted in the middle of the downloading operation. Such downloading also requires the line to be occupied for a long time. In addition, the amount of bio-related information is increasing at such a rapid pace that it is expected that the downloading operation would be more and more time-consuming and complicated. Further, as the information in the open databases are managed by individual database administrators, it has been difficult for the biology researchers to be constantly informed of the update period or the current number of data items in the individual open databases.

There are also various links between databases. Accordingly, data search has been conducted by tracking a plurality of links. For example, as shown in FIG. 22, when obtaining data in a database D that corresponds to data in a database A, there are a route that goes through a database B and another route that goes through a database C. Data in the database B that corresponds to a gene A1 in the database A are B1 and B2, to which data D1 and D2 in the database D correspond. Data in the database C that corresponds to the gene A1 is C1, to which data D3 in the database D corresponds. In this example, there are three items of data D1, D2 and D3 in the database D that correspond to the gene A1 in the database A, so the user has to re-examine which is the correct data.

In light of the above-described problems associated with the search on databases regarding information about biological substances, it is the object of the invention to provide a method and system for enabling data in databases on the network to be easily retrieved.

In accordance with the invention, necessary information is extracted from a plurality of databases to create an index, which is then distributed. Thus, the user can obtain only necessary information. As a plurality of items of data are put together in a single index, the amount of data can be reduced and the download from the data center to the user facility can be smoothly carried out, so that the problem of the line being occupied during download for a long time can be avoided. Furthermore, as the updating of the databases and changes in format, for example, can be effected together at the data center, the user can be spared of bothersome work required for those purposes. In cases where there are no chances of information leakage, for example, the user may directly access an index placed at the data center and conduct a search without downloading it into the user facility.

The invention provides a data distribution method comprising the steps of: downloading data from a plurality of databases in which information about biological substances is stored; extracting from the downloaded data information indicating a link between data in two databases, a detailed description of each data, and sequence data for homology search, which together constitute an index; and distributing the thus extracted index.

The invention also provides a data search method comprising the steps of: downloading data from a plurality of databases in which information about biological substances is stored; extracting from the downloaded data information indicating links between data in two databases; receiving a start database name, a target database name, and a data ID in the start database, which together constitute a search key; acquiring a data ID of the target database by following those links among the extracted links between data that match the predetermined order of the link between a plurality of databases, while referring to information indicating the predetermined order of the link between the databases and using the received data ID in the start database as a start point; and displaying the thus acquired data ID of the target database.

The invention further provides a data search method comprising the steps of: downloading data from a plurality of databases in which information about biological substances is stored; extracting from the downloaded data information indicating links between data in two databases and sequence data for homology search; receiving a start database name, a target database name, and input sequence data, which together constitute a search key; conducting a homology search for homology-search sequence data in the start database, using the input sequence data; acquiring a corresponding data ID of the target database by following those links among the extracted links between data that match the predetermined order of a link between databases, while referring to information indicating the predetermined order of the link between the databases and using as a start point the data ID in the start database that has been acquired by the homology search; and displaying the thus acquired data ID of the target database.

The invention further provides a data search method comprising the steps of: preparing index data that is a collection of information indicating links between data in two databases, based on a plurality of databases in which information about biological substances is stored; preparing a table defining the order of the links between the plurality of databases; receiving a start database name, a target database name, and a data ID of the start database, which together constitute a search key; acquiring a corresponding data ID in the target database by following those links among the links between data that match the order of the links between the databases, while using as a start point the data ID in the start database that has been received; and displaying the acquired data ID of the target database.

The invention further provides a data search method comprising the steps of: preparing index data that is a collection of information indicating links between data in two databases and sequence data for homology search, based on a plurality of databases in which information about biological substances is stored; preparing a table defining the order of links between the plurality of databases; receiving a start database name, a target database name, and input sequence data, which together constitute a search key; conducting a homology search for homology-search sequence data in the start database, using the input sequence data; acquiring a corresponding data ID of the target database by following those links among the links between the data that match the order of the links between the plurality of databases, using as a start point the data ID in the start database that has been acquired by the homology search; and displaying the acquired data ID of the target database.

The invention further provides a data search system comprising: index data that is a collection of information indicating links between data in two databases that is gathered from a plurality of databases in which information about biological substances is stored; a table defining the order of the links between the plurality of databases; an input portion for receiving a start database name, a target database name, and a data ID in the start database, which together constitute a search key; a search portion for acquiring a corresponding data ID of the target database by following those links among the links between data that match the order of the links between the databases, while using as a start point the data ID in the start database that has been received; and a display portion for displaying the acquired data ID of the target database.

The invention moreover provides a data search system comprising: index data that is a collection of sequence data for homology search and information indicating links between data in two databases that is gathered from a plurality of databases in which information about biological substances is stored; a table defining the order of the links between the plurality of databases; an input portion for receiving a start database name, a target database name, and an input sequence data in the start database, which together constitute a search key; a first search portion for conducting a homology search for homology-search sequence data in the start database, using the input sequence data; a second search portion for acquiring a corresponding data ID of the target database by following those links among the links between data that match the order of the links between the plurality of databases, using as a start point the data ID in the start database that has been acquired by homology search; and a display portion for displaying the acquired data ID of the target database.

In accordance with the inv*, a search can be conducted on thousands of data items against an index all at once. Further, by classifying and arranging the databases with which a network is constructed by living species (humans, mice, rice, for example) and by the type of data (DNA, mRNA, EST), the user can obtain data matched with his purposes. By preparing a table or the like defining the order of links among a plurality of databases, and by following the links between the plurality of databases according to the defined route, search result with a reduced amount of noise can be obtained.

BRIEF DESCRIPTION OF THE DRAWINGS

FIG. 15 shows an example of input data.

FIG. 16 shows an example of the screen of a display portion on which search result is displayed.

FIG. 18 shows an example of an input data file.

FIG. 20 shows an example of display of homology search result.

DESCRIPTION OF THE PREFERRED
EMBODIMENTS

The invention will be hereafter described by way of embodiments with reference made to the drawings.

Figure 1:
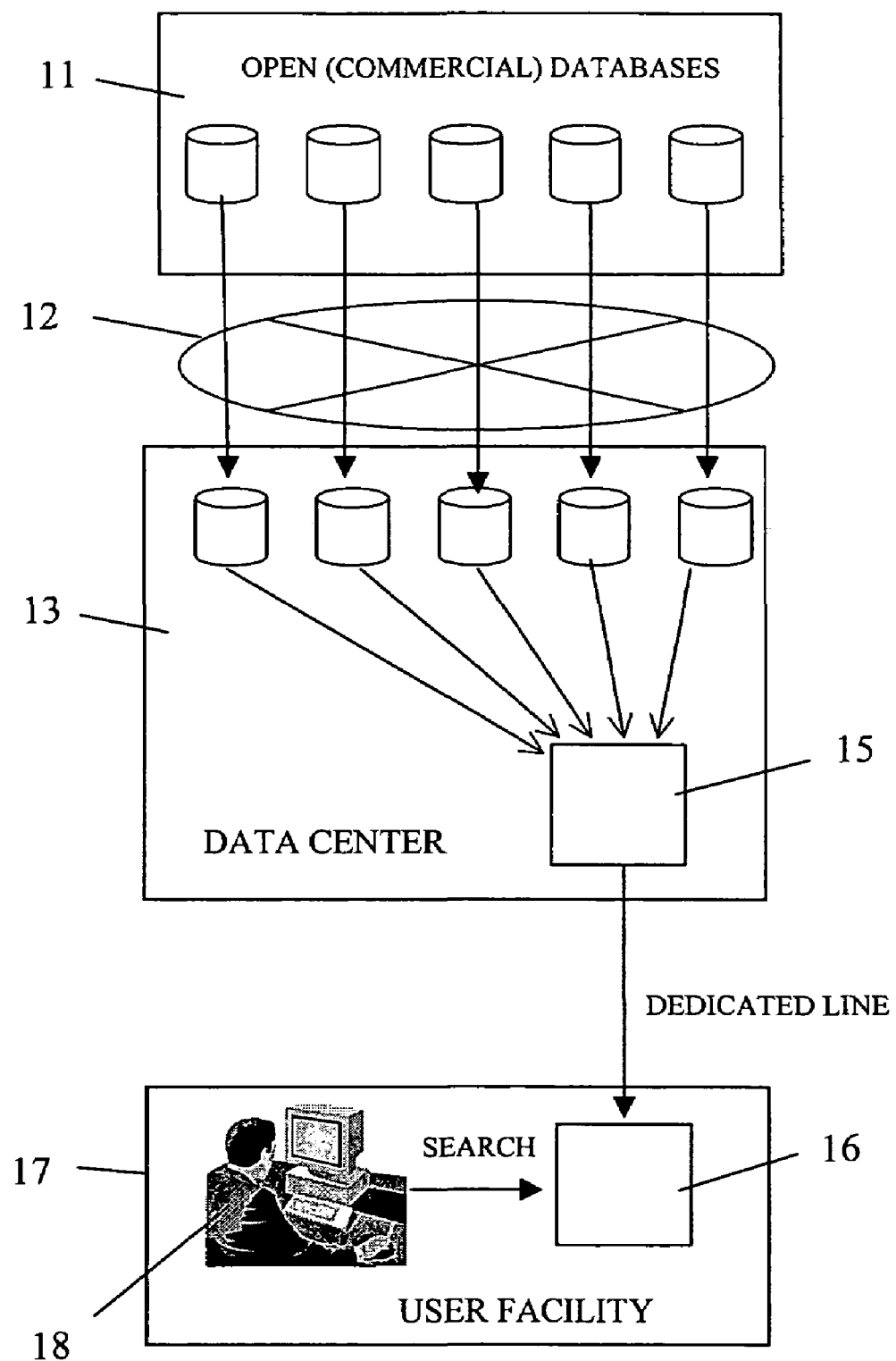
FIG. 1 is a conceptual chart showing an example of the structure of the biological substance information search system according to the invention.

FIG. 1 is a conceptual chart of an example of the structure of the biological substance information search system according to the invention. Data in an open or commercial database 11 is downloaded to a data center 13 via the Internet 12. In the data center 13, an index 15 is created based on the downloaded data. The thus created index 15 is delivered (index 16) to a facility 17 of the user 18, who conducts a search on the index 16.

The index includes link information indicating the correspondence among data contained in different databases, detailed description of each data, and homology-search data. The detailed description of each data refers to the detailed description of entries stored in each entry in the database. The homology-search data refers to information about sequences such as base sequence or protein sequence contained in the database. The user conducts a homology search between the base sequence or protein sequence he possesses and the base sequence or protein sequence in the data of a target open database. The homology search usually employs software called BLAST. Thus, for the data subjected to homology search, a FASTA-format sequence data is usually formatted for BLAST.

By classifying and organizing the databases employed in constructing the network by the living species (humans, mice and rice, for example) and by the type of data (DNA, mRNA, EST), the user can obtain data according to his purposes.

Figure 2:
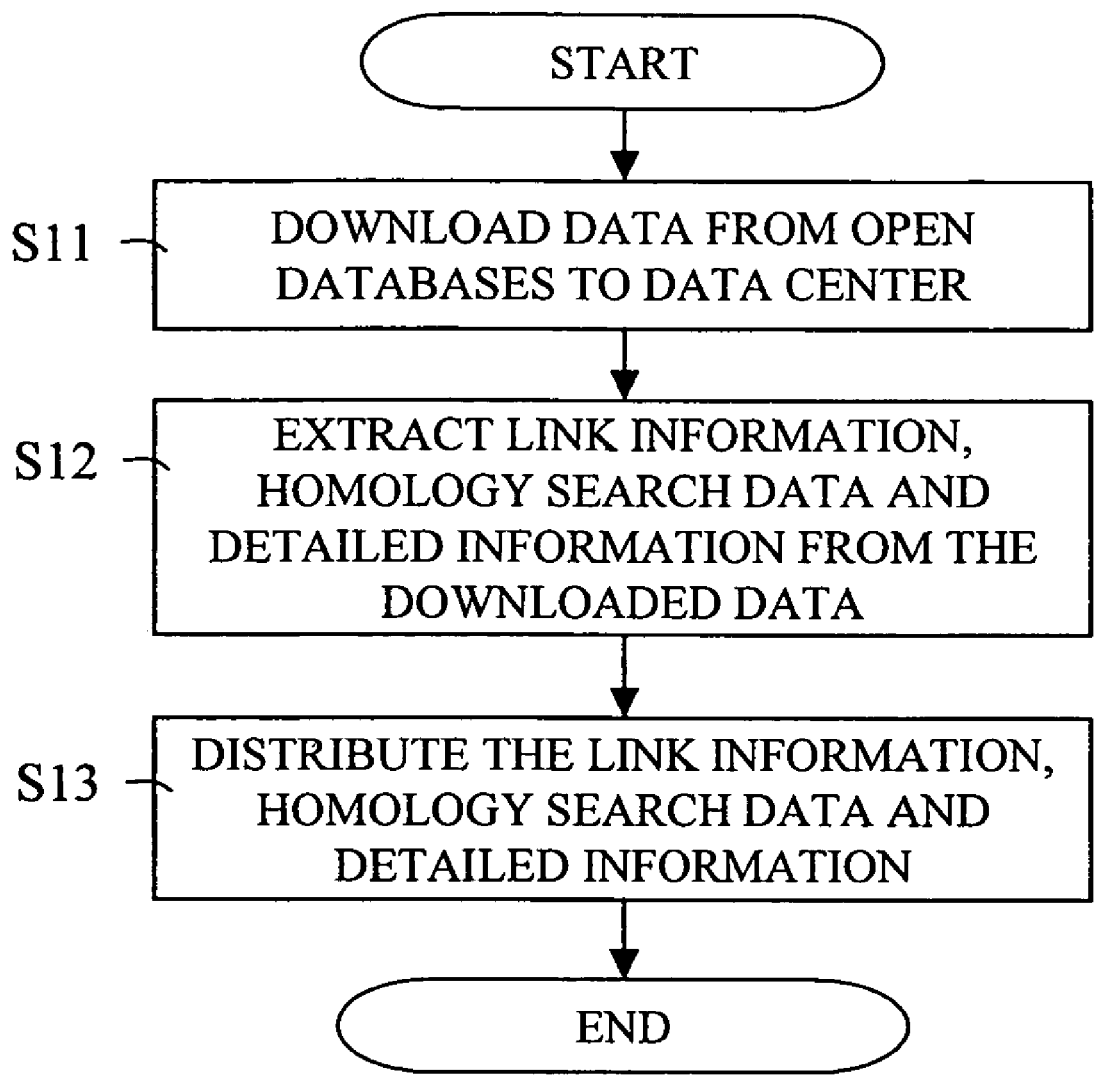
FIG. 2 shows a flowchart of the procedure for creating an index for retrieving information, based on a plurality of database in which biological substance information is stored.

FIG. 2 shows a flowchart of the procedure for creating the index for information search, based on a plurality of databases storing information about biological substances.

In step 11, data is downloaded from the open databases, such as official databases and commercial databases, to the data center. In step 12, the link information, homology-search data, and the detailed description of each ID are automatically extracted from the downloaded data. The homology search data is obtained from all databases to be registered in the index in which sequence information exists. The detailed information is obtained from all of the databases to be registered in the index. Finally, in step 13, the link information, homology search data and the detailed description of each ID are together delivered to the user's facility.

Figure 3:
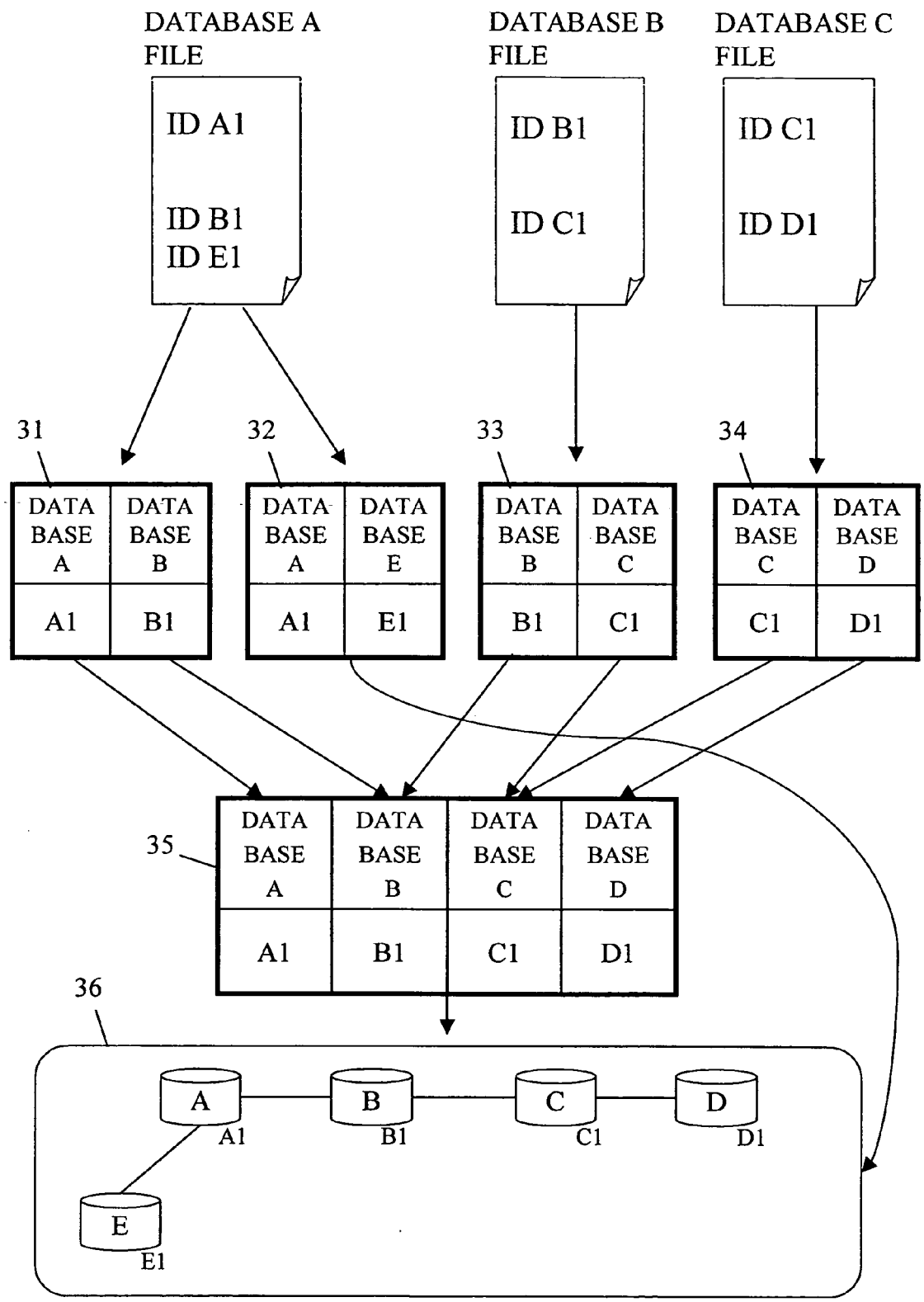
FIG. 3 shows a procedure for creating link information.

FIG. 3 illustrates the procedure for creating the link information in step 12 of FIG. 2. In the illustrated example, a database A corresponds to databases B and E such that an entry A1 in the database A corresponds to an entry B1 in the database B and an entry E1 in the database E. These correspondences are described in a database A file. Thus, individual IDs are taken out of the database A file, and A1 in the database A and B1 in the database B are stored in a table 31. Similarly, there is described the correspondence between the entry A1 in the database A and the entry E1 in the database E, and therefore this correspondence is stored in a table 32. A database B file describes the correspondence between the entry B1 in the database B and an entry C1 in a database C, which are taken out and stored in a table 33. A database C file describes the correspondence between the entry C1 in the database C and an entry D1 in a database D, which are taken out and stored in a table 34. By combining these tables 31, 33 and 34, a table 35 can be created. The tables 32 and 35 can be schematically described by way of a link chart shown in FIG. 36.

Figure 4:
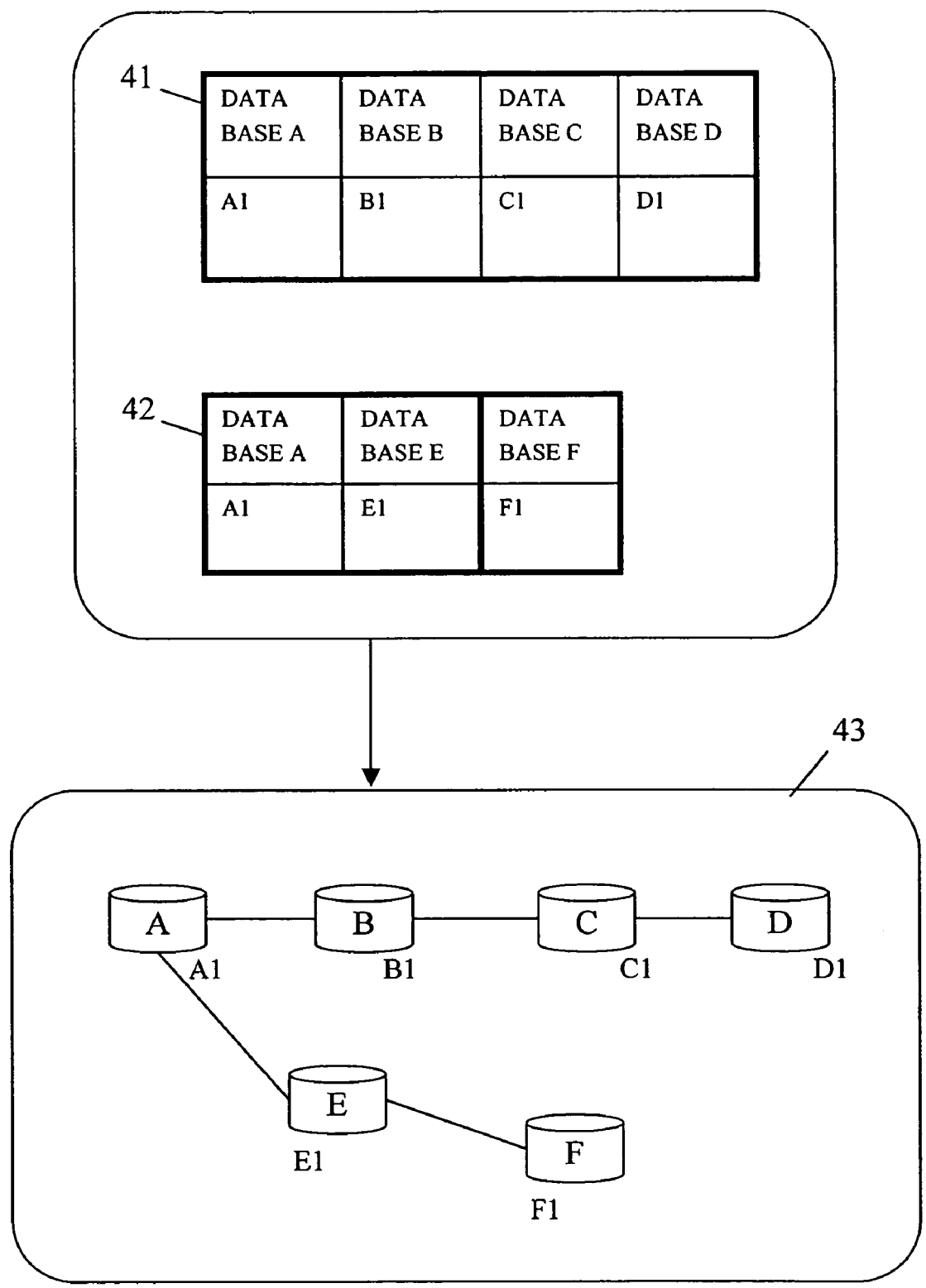
FIG. 4 shows another example of routes obtained from the link information.

FIG. 4 shows another example of the route obtained from the link information. In the tables stored in the databases as link information, the IDs of two databases are associated with each other, as shown in the tables 31 to 34 in FIG. 3. Based on these tables, a table 41 or 42 is created, as shown in FIG. 4. The relationship between these tables can be described by way of a link chart 43. By tracing the corresponding data on the link chart 43, the data D1 in the database D that corresponds to the data A1 in the database A, for example, can be retrieved.

The databases contain link information linking them to other various databases. As a result, the problem described above with reference to FIG. 22 could occur due to complications among the links. Thus in the present invention, the links among the databases are limited such that the individual databases are linked to one another according to a predetermined rule (order). This limitation imposed on the links among the databases will be described below.

Figures 5, 6:
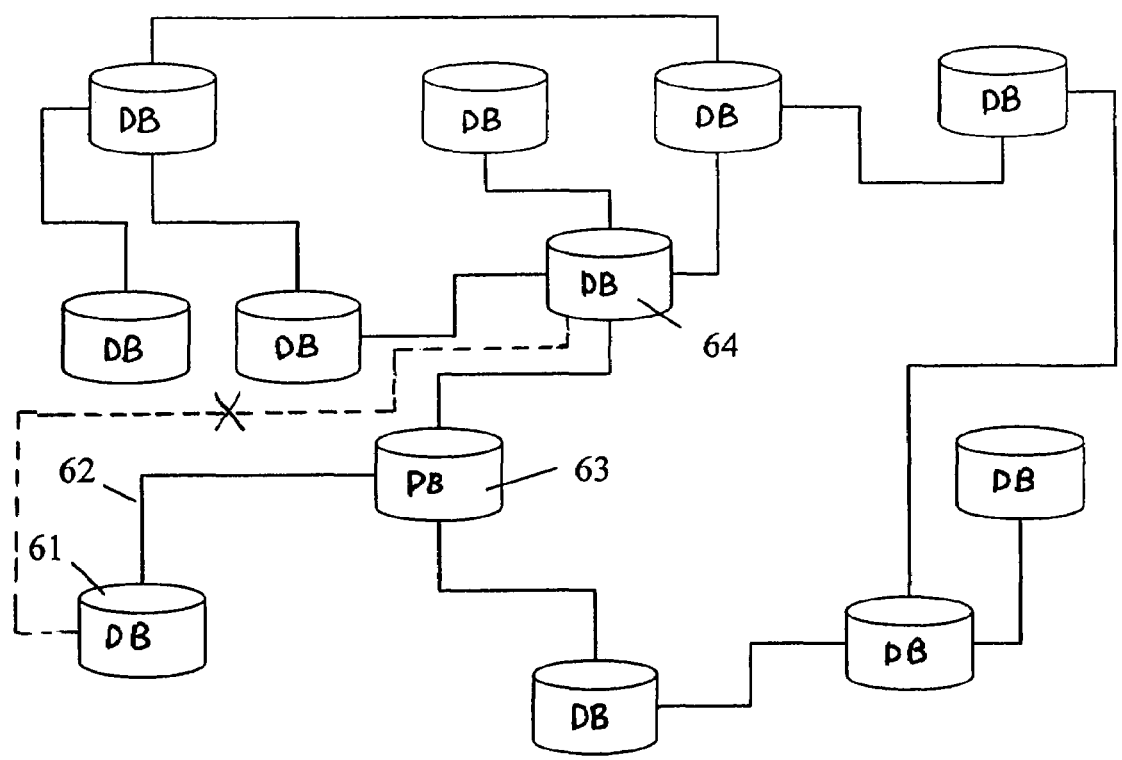
FIG. 5 shows an example of a route table in which information about routes (order) of links among databases is stored.
FIG. 6 shows an example of a network display of the contents of the route table.

FIG. 5 shows an example of a route table in which information concerning the permitted routes (order) among the databases is stored. "KeyDB" designates a database as a search starting point. "TargetDB" designates a database to be searched for data corresponding to data in KeyDB. The databases A, B, C, and so on including open databases, commercial databases and private databases, may in some cases describe inter-data linkage information indicating to which data in other databases certain data in a particular database corresponds. In such cases, it is possible to follow various routes to search for the data in TargetDB that corresponds to designated data in KeyDB. However, if all of the link information is to be utilized, there is a chance of picking up noise information, as mentioned above. Therefore, the route (order) of the link from KeyDB to TargetDB, once KeyDB and TargetDB are designated, is uniquely designated by the route table. In the illustrated example, in the case where KeyDB is A and TargetDB is C, the data in the database C that corresponds to data in the database A is retrieved by following the link in the order of the database A, database B and database C, referring to the route table of FIG. 5. Similarly, when KeyDB is A and TargetDB is D, the data in the database D that corresponds to data in the database A is retrieved by following the link in the order of the database A, database B, database C and database D, while referring to the route table of FIG. 5.

FIG. 6 shows an example of the contents of the route table by way of a network. The fact that databases 61 and 63 correspond to each other is indicated by a line 62 connecting these two databases. It is now assumed that the database 61 has been newly created on the basis of the data stored in the database 63, and that data A stored in the database 61 corresponds to data B stored in the database 63. In the present invention, only such link information that follows the origin of the data is utilized, and even if link information is stored in the database 61 that is related to another database 64, such information is not utilized as the link information for retrieval. By thus limiting the link between databases, the acquisition of unnecessary data can be limited.

Figure 7:
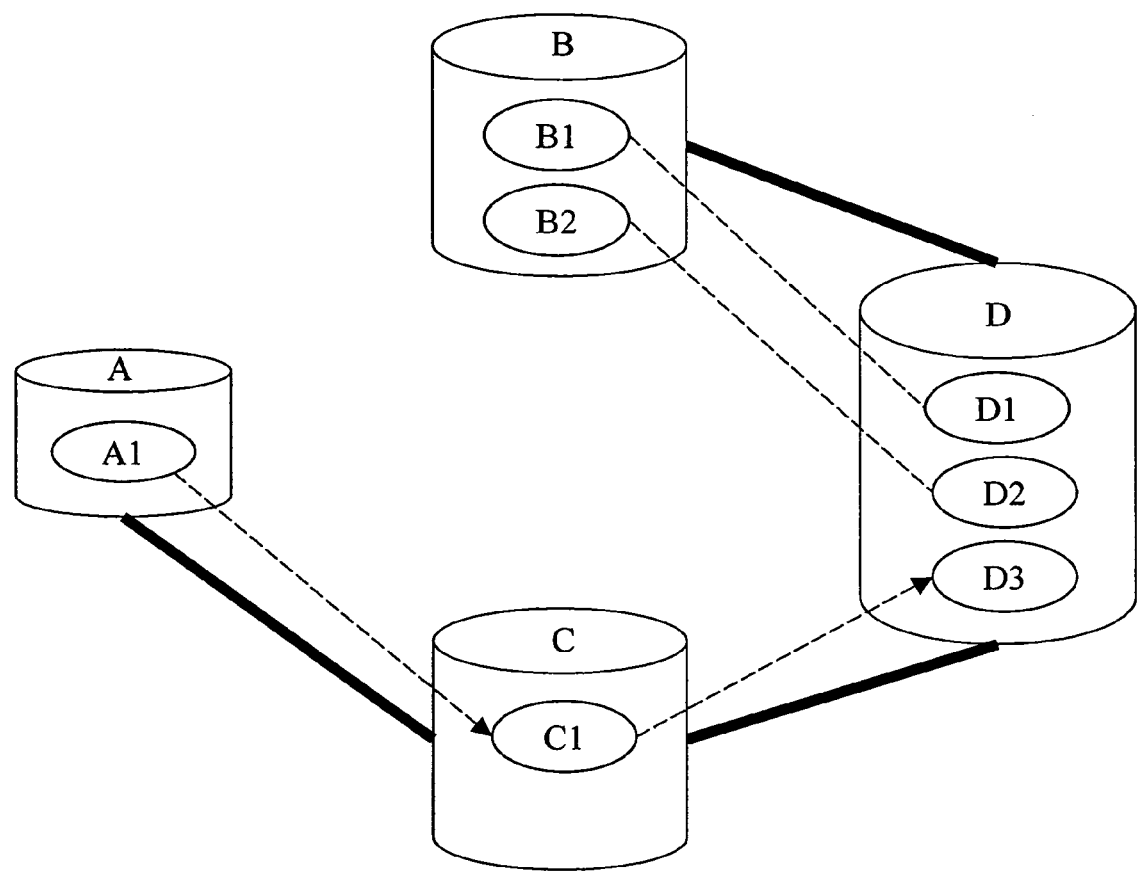
FIG. 7 illustrates the effect of limiting the links among databases.
Figure 22:
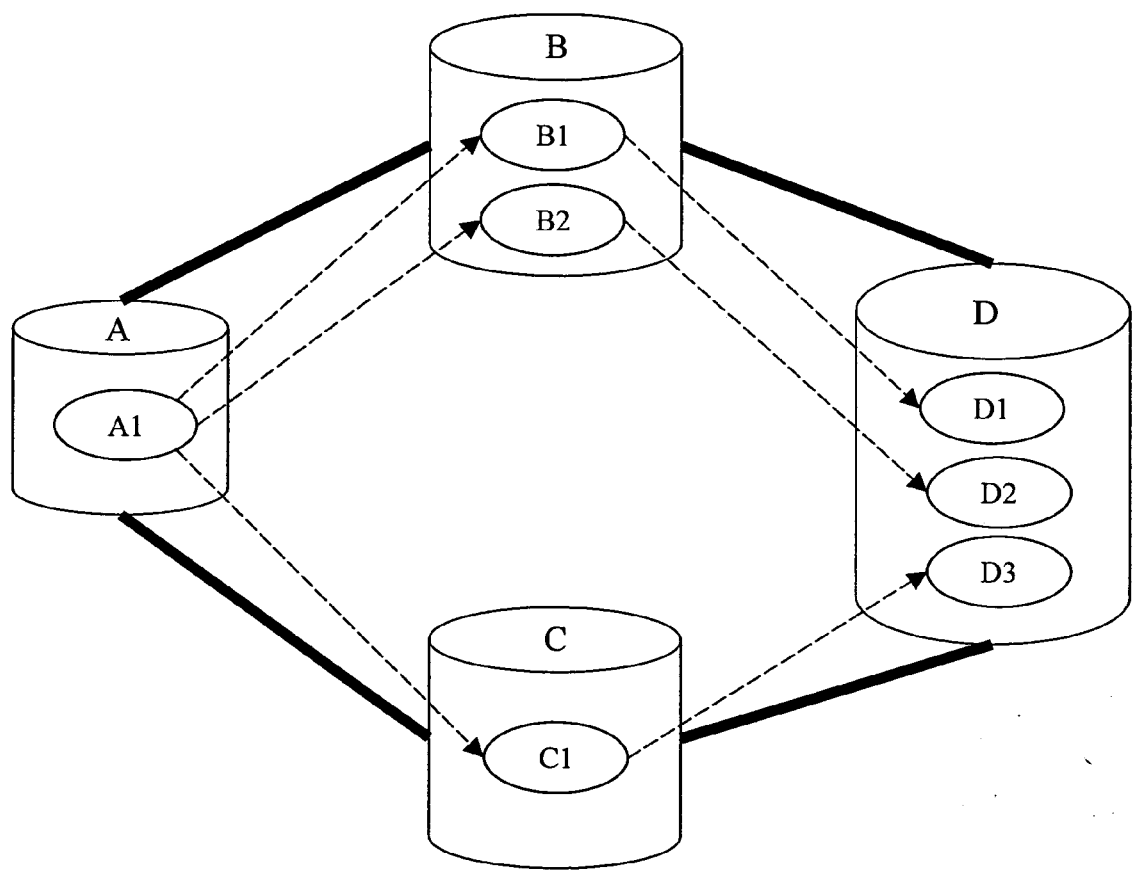
FIG. 22 shows an example of conducting a search by following a plurality of links.

FIG. 7 shows the effect of limiting the link between databases, the figure corresponding to FIG. 22.

In the case where the database A describes link information to the database B and link information to the database C, the present invention utilizes only the link information between the database A and the database C, which is more reliable, and does not utilize the link information between the database A and the database B. As a result, gene data D3 in the database D that corresponds to gene data A1 in the database A can be acquired. Thus, by limiting the link between the databases, the acquisition of unwanted data that produces noise, as described with reference to FIG. 22, can be limited, so that only appropriate data can be acquired.

Figure 8:
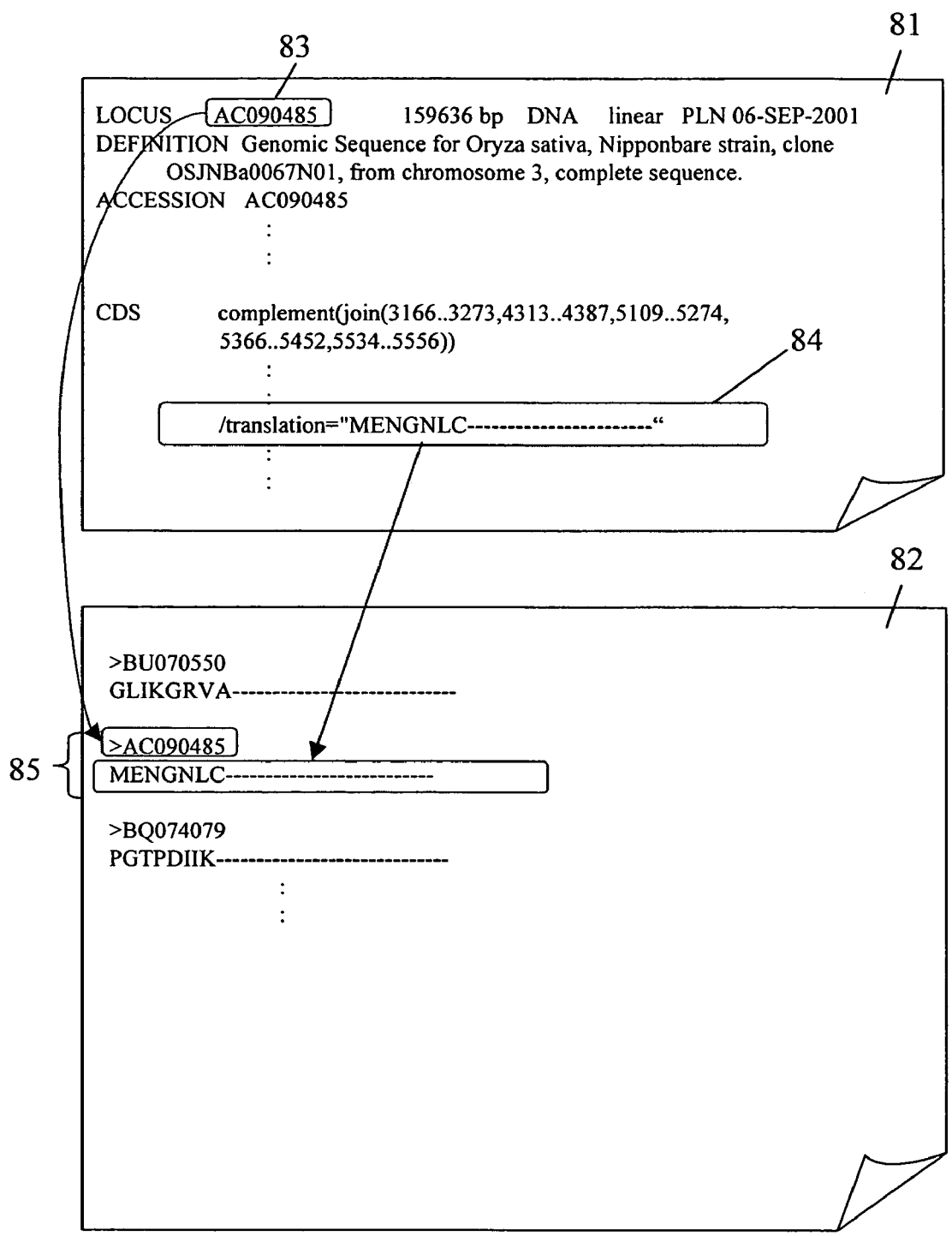
FIG. 8 shows a procedure for creating homology search data.

FIG. 8 shows the procedure for creating the homology search data in step 12 of FIG. 2. In the illustrated example, an ID 83 and sequence data 84 for each entry are extracted from a file 81 downloaded from an open database, and a file 82 in which sequence data 85 of FASTA format is stored is created.

Figure 9:
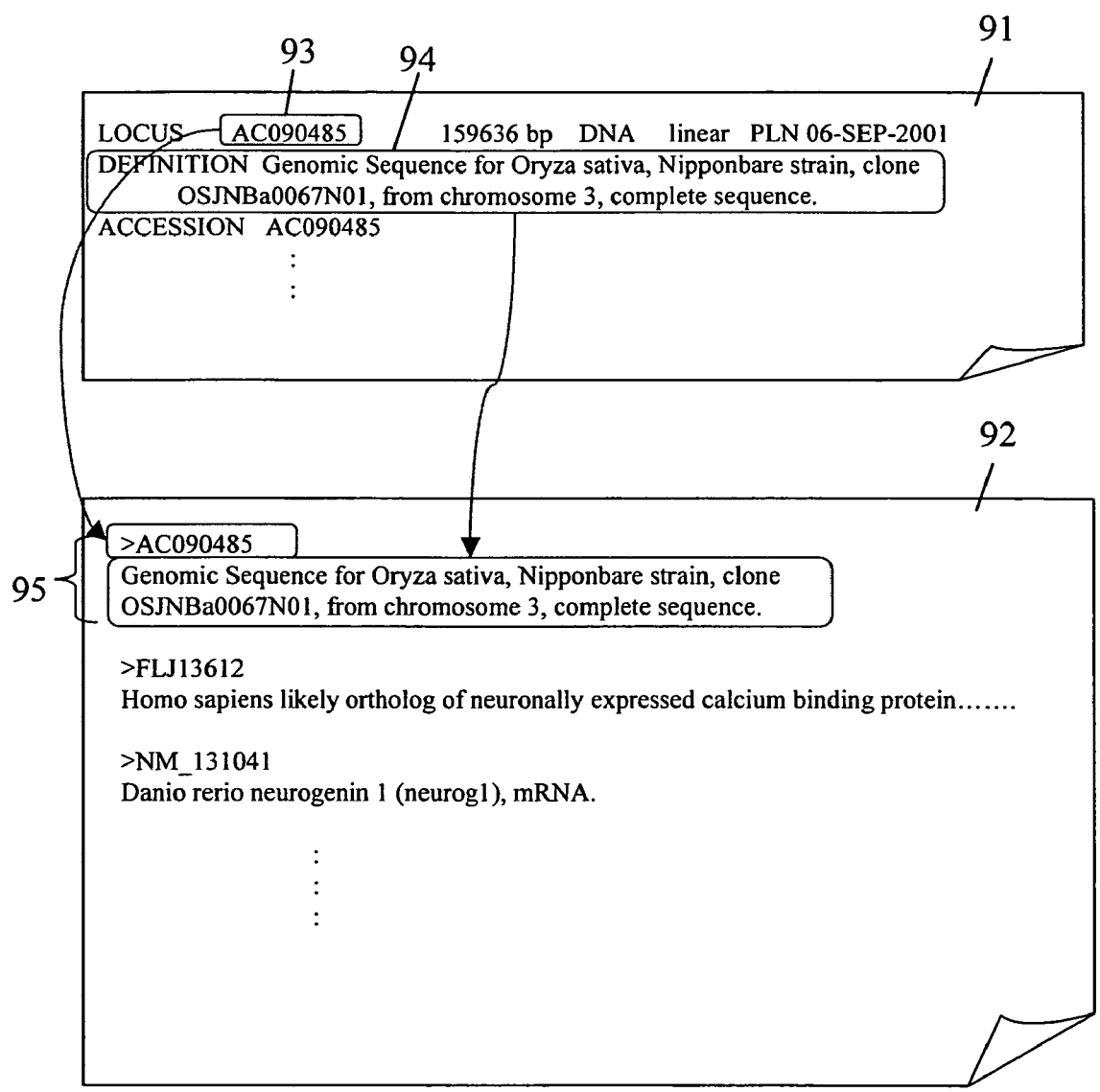
FIG. 9 shows a procedure for creating a detailed description file.

FIG. 9 shows the procedure for creating a detailed-description file in step 12 of FIG. 2. In the illustrated example, an ID 93 for each entry and a detailed description 94 concerning the entry are extracted from a file 91 downloaded from an open database, and they are then stored in a detailed-description file 92 as a pair 95 of the ID and the detailed description.

Figure 10:
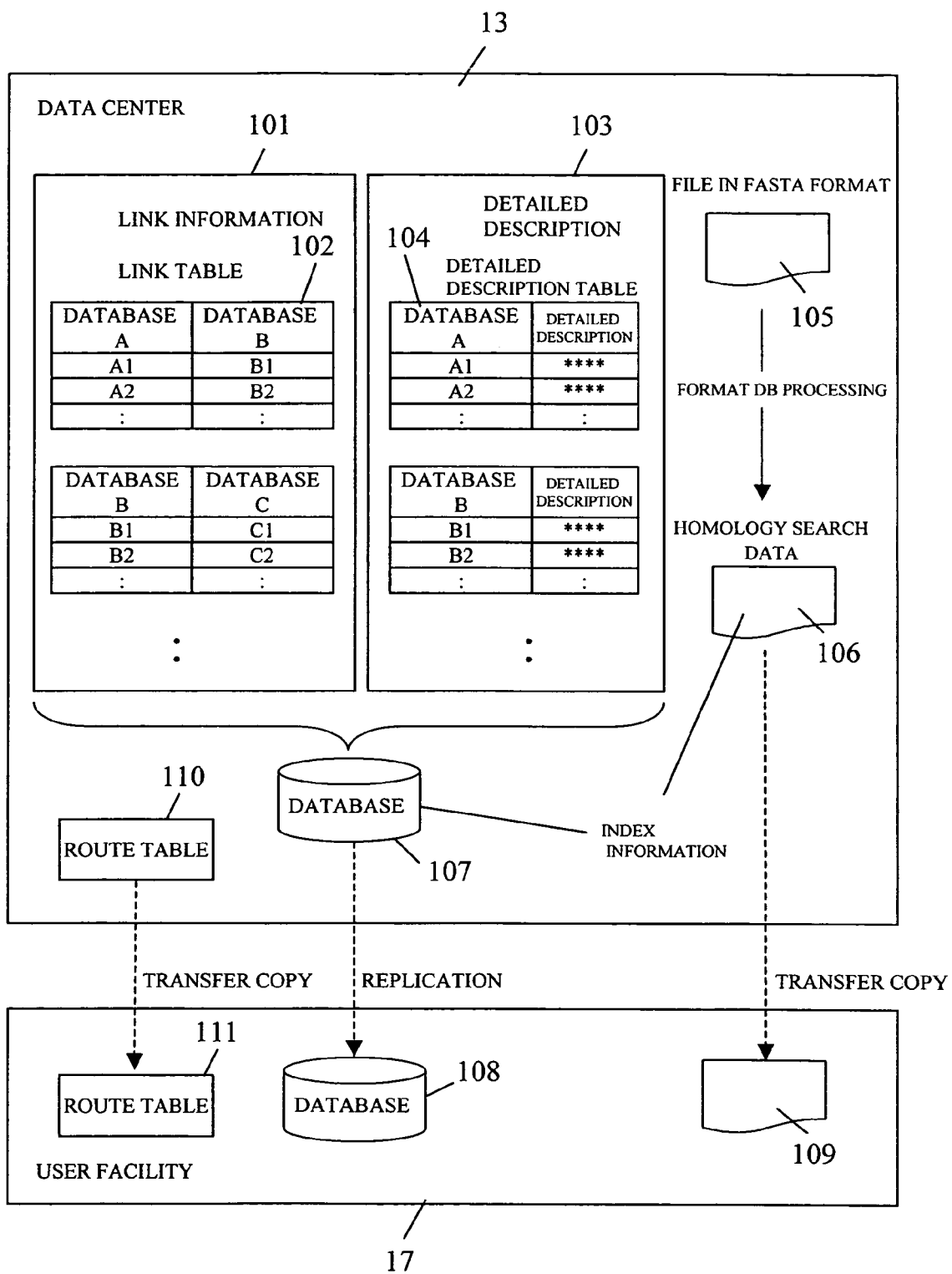
FIG. 10 shows the details of index information.

FIG. 10 shows the details of the index information. The index information (link information 101, detailed description 103, and homology search data 106) is created in the data center 13. The link information 101 is retained in the form of link tables 102. The detailed description 103 is retained in the form of detailed description tables 104. The individual tables of the link information and detailed description are stored in a database 107. A file 105 of FASTA format is formatted for BLAST, thereby creating homology search data 106. The index information thus created in the data center 13 is transferred to a user facility 17. In this case, a copy of the database 107 is created in a database 108 in the user facility 17 by a replication process. Further, a copy 109 of the homology search data 106 is transferred to the user facility 17. Also, a copy 111 of a route table 110 in which information about the route (order) of the links among the databases is stored is transferred to the user facility 17.

Figure 11:
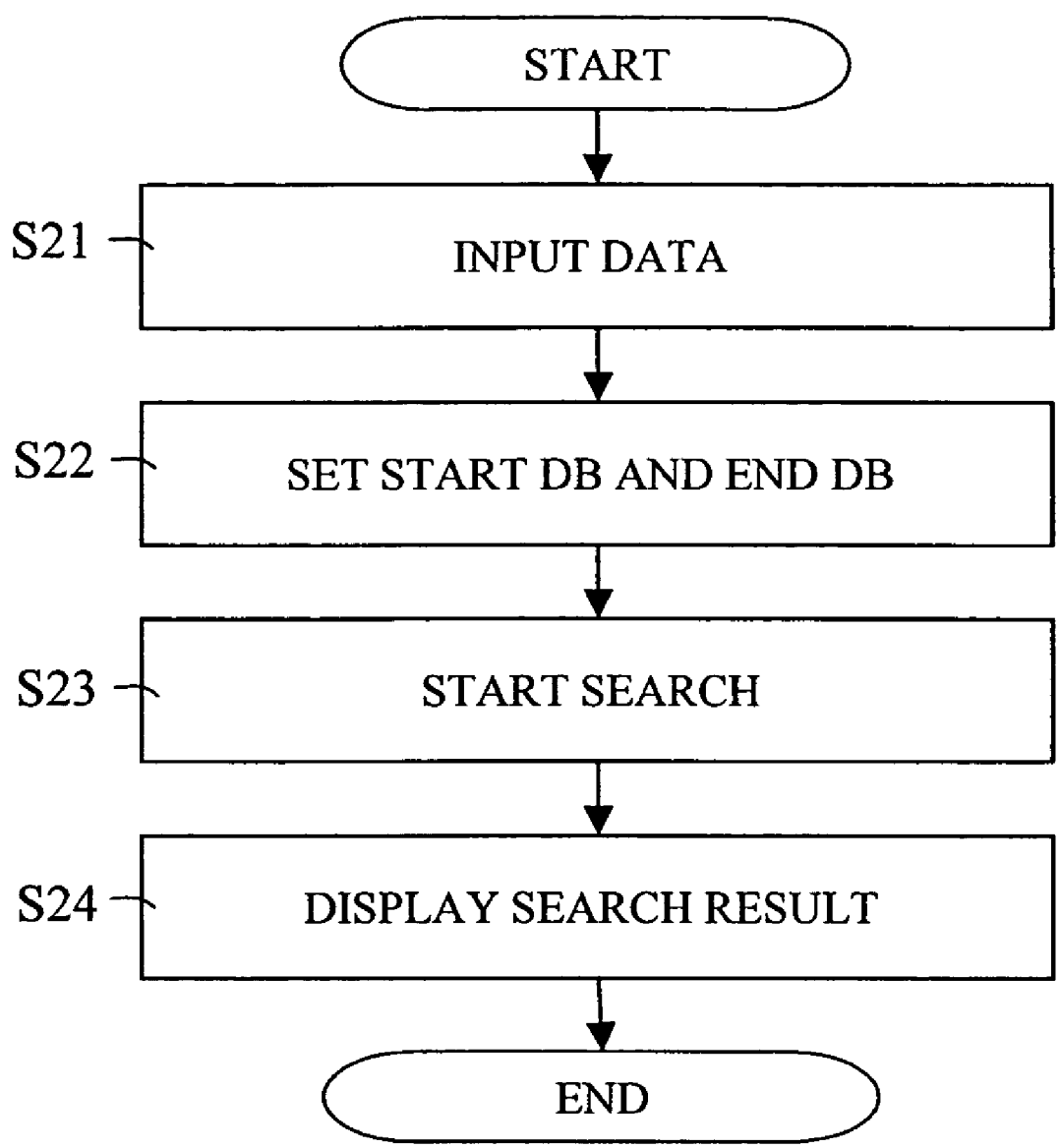
FIG. 11 shows a flowchart of the procedure for biological substance information search according to the invention.
Figure 12:
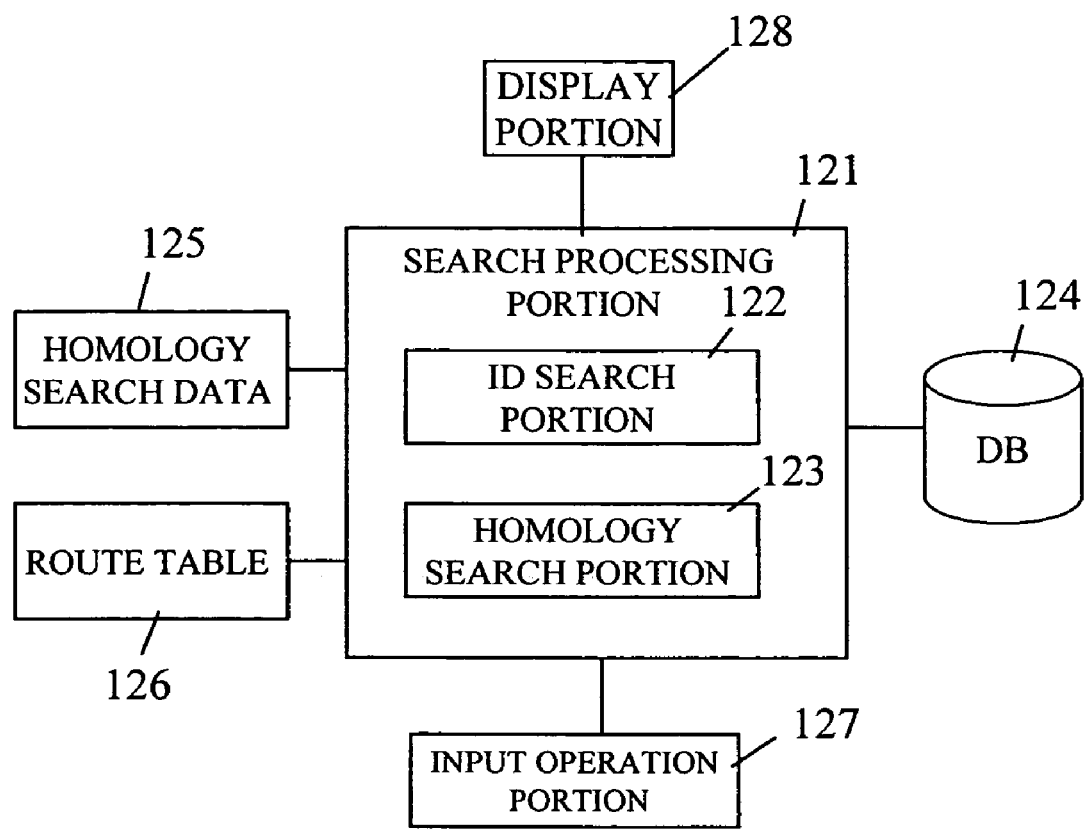
FIG. 12 shows a block diagram of the search system according to the invention.

FIG. 11 shows a flowchart of the procedure for biological substance information search according to the invention. FIG. 12 shows a block diagram of a search system for realizing this search method.

Figure 13:
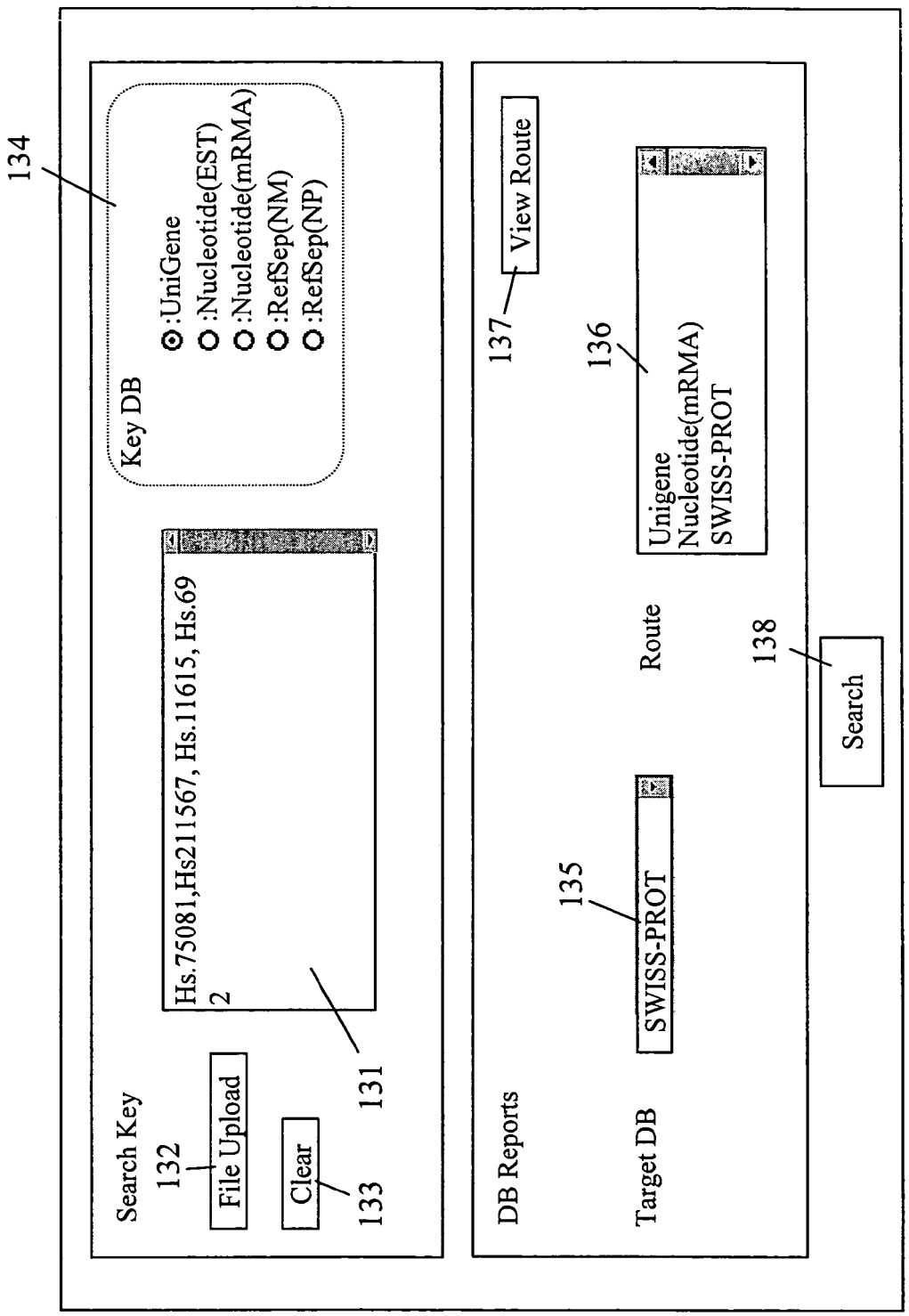
FIG. 13 shows an example of an interface used when searching for the ID of a database.
Figure 14:
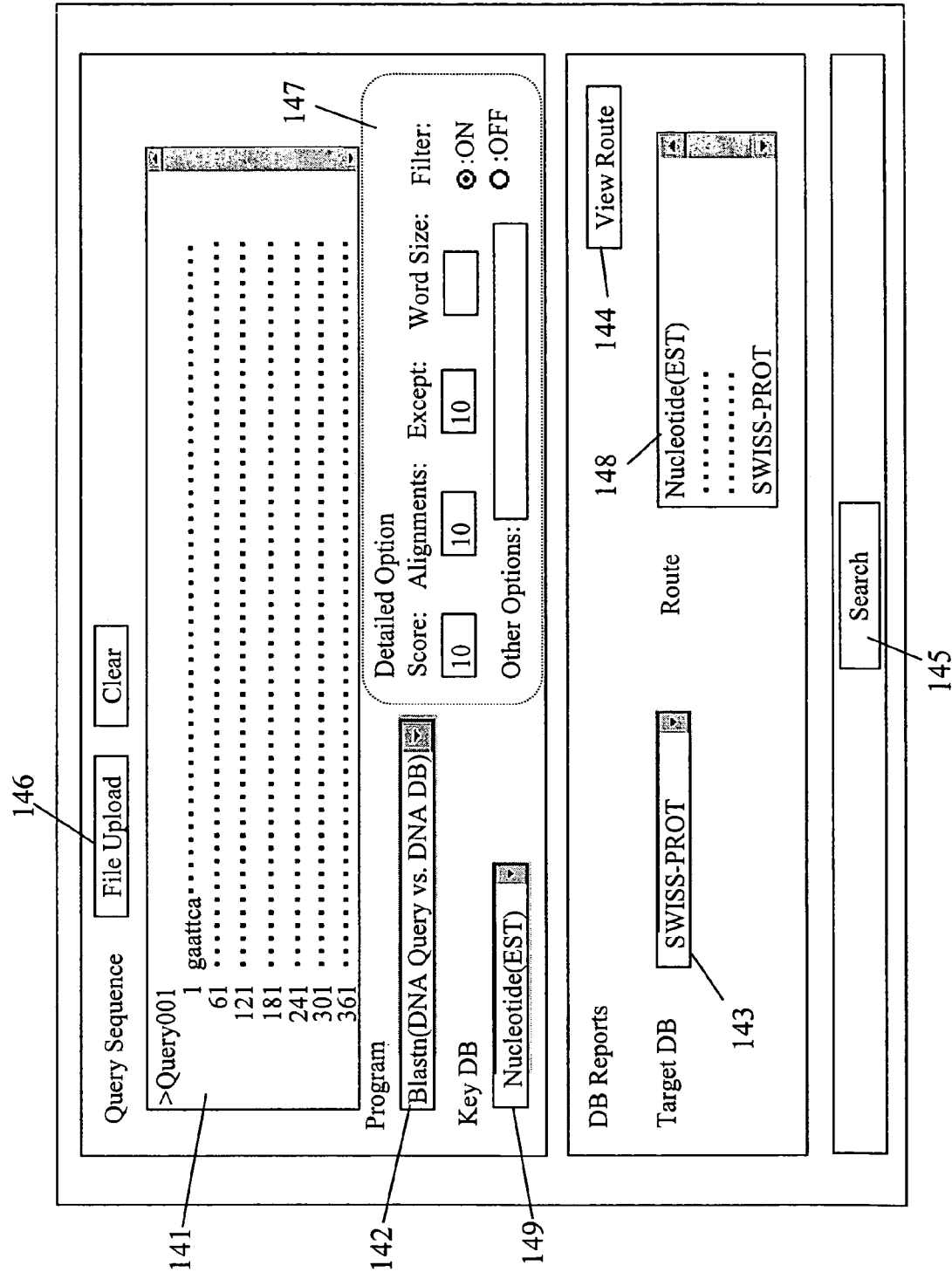
FIG. 14 shows an example of an interface used when searching for a sequence.

The search system of the invention includes a database 124 in which the link information and detailed description described with reference to FIG. 10 are stored, homology search data 125, a route table 126 describing the order of links among databases, an input operation portion 127, a display portion 128 for displaying search results, and a search processing portion 121. The search processing portion 121 includes an ID search portion 122 for conducting ID search by following the links, and a homology search portion 123 for conducting homology search between sequence data inputted from the input operation portion and homology search data. FIGS. 13 and 14 illustrate examples of an input interface used during data search. FIG. 13 shows the input interface used when searching for the ID of a database, and FIG. 14 shows the input interface used when searching for a base sequence or a protein sequence.

First, the search method and system whereby the ID of user data is converted into the ID of a database on the network will be described.

Figure 15:
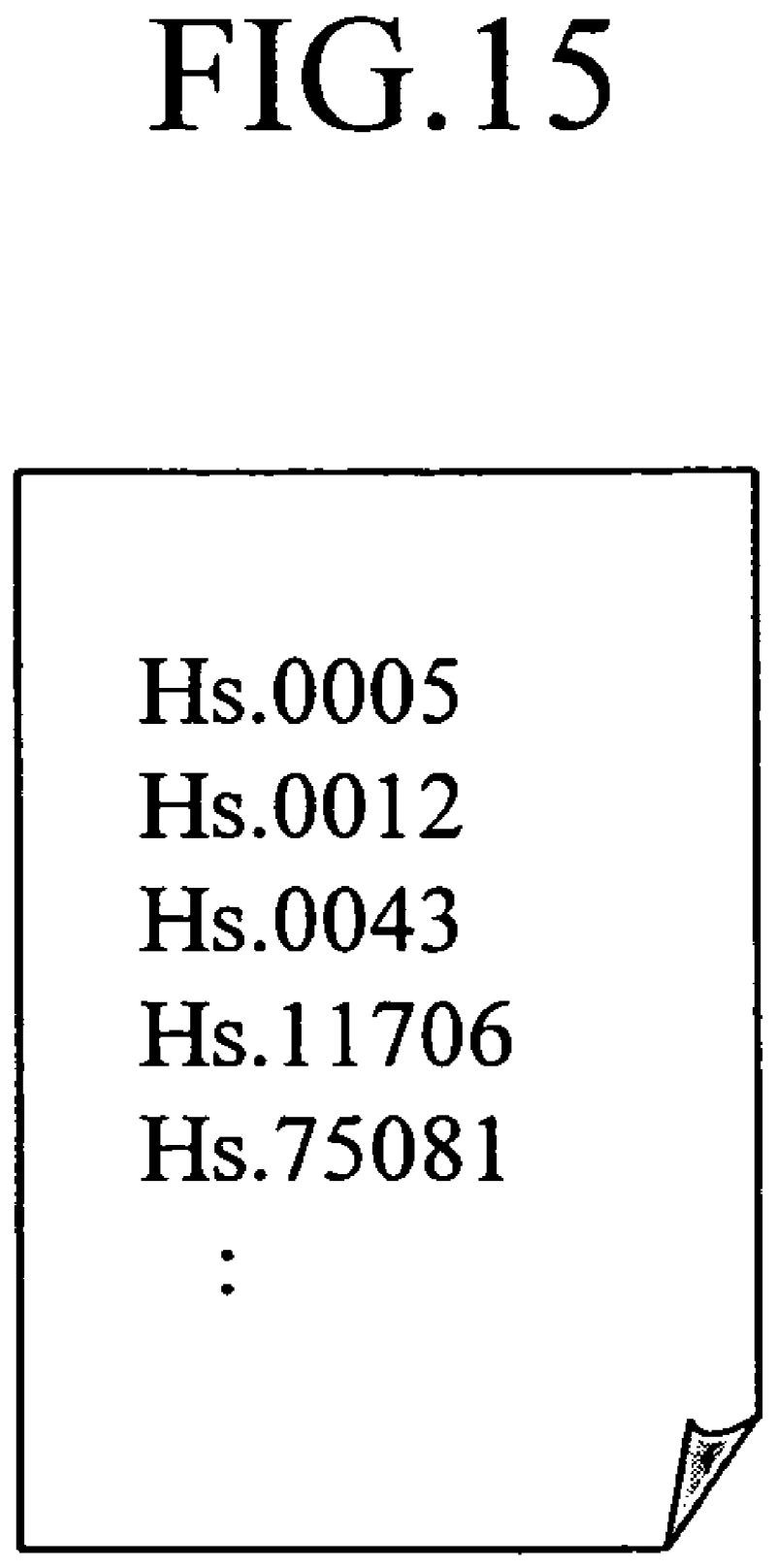

In step 21 of FIG. 11, the input operation portion 127 is operated to input data. For example, as an input-data file as shown in FIG. 15 is selected by a "File Upload" button 132 shown on the screen of FIG. 13, the data is displayed in a data input field 131 shown in FIG. 13, separated by commas. The input data can be cleared by depressing a "Clear" button 133.

The input data example shown in FIG. 15 is UniGene data publicly available from NCBI.

In step 22 of FIG. 11, KeyDB and TargetDB are set. A database with the same ID as that of the input data is selected from a KeyDB list 134 shown in FIG. 13, and a database as the object of conversion is selected from a TargetDB list 135 of FIG. 13. Then, a search route is displayed in a field 136 by referring to the route table 126. As a button 137 is selected, the entire view of the ID network as shown in FIG. 6 is displayed, where the KeyDB and TargetDB can be confirmed.

Then, in step 23, a search start button 138 is depressed to start a search. A search program in the ID search portion 122 follows the designated search route to search for a data ID of TargetDB that corresponds to the data ID of KeyDB that has been inputted.

Figure 17:
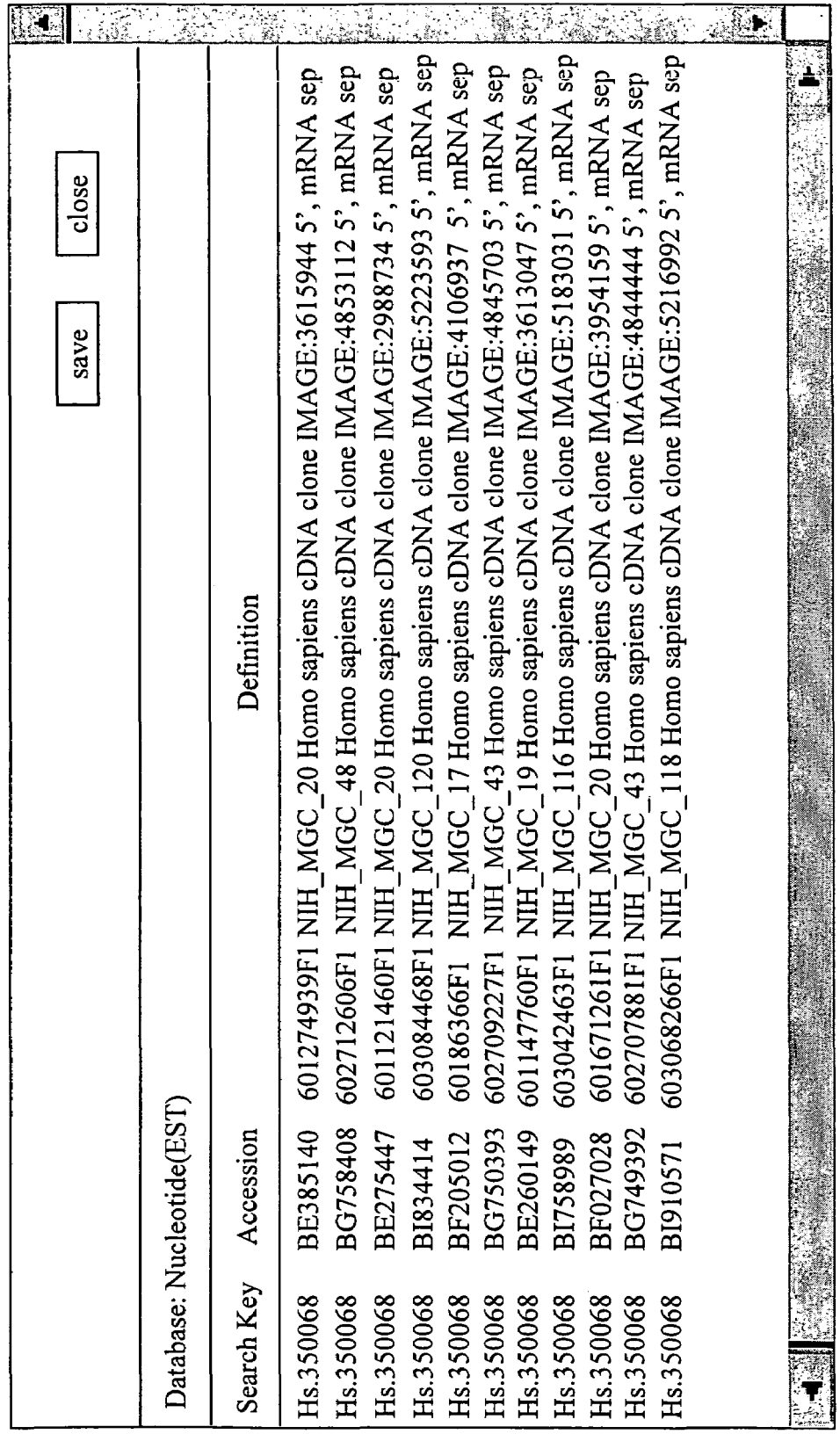
FIG. 17 shows an example of display of detailed description.

The routine then proceeds to step 24, in which the search result is displayed. FIG. 16 shows an example of the display screen of the display portion 128 on which the search result is displayed. In the illustrated example, entries 163 in SWISS-PROT, which is Target DB, that correspond to entries 162 in UniGene, which is KeyDB, are shown in a field 161. In "Hit Count" 166, the number of the entries 163 in TargetDB that correspond to the entries 162 in KeyDB is shown. By clicking a KeyDB button or TargetDB button 164, a detailed description shown in FIG. 17 is displayed. By clicking a "View Route" button 165, a chart showing the search route among databases as shown in FIG. 6 is displayed.

Next, an example where a base sequence or protein sequence the user wishes to search for is converted into the ID of a database on the ID network will be described.

Figure 18:
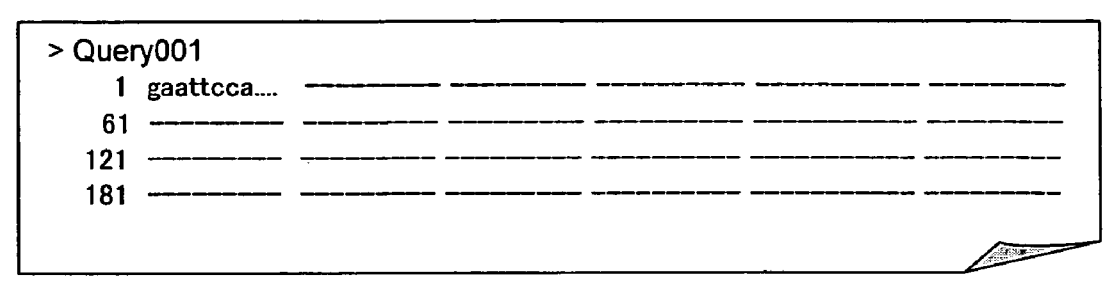

In step 21 of FIG. 11, the sequence data to be retrieved is inputted via the input operation portion 127. For example, as a "File Upload" button 146 on the input screen of FIG. 14 is clicked and an input data file shown in FIG. 18 is selected, the input sequence data is displayed in a data input field 141 of the input screen. By clicking the "Clear" button, the data input field 141 can be emptied.

The routine then advances to step 22, where KeyDB and TargetDB are set. A database (KeyDB) that is desired to be associated with the search data is selected from a DB list 149 in the input screen shown in FIG. 14, and a target database (TargetDB) as the object of conversion is selected from a TargetDB list 143 of FIG. 14. After KeyDB is set, an appropriate BLAST technique is selected from a program list 142, depending on whether the sequence data to be retrieved and the data stored in the database as KeyDB are nucleotide sequences or protein sequences. For example, "blastn (DNA Query vs. DNA DB)" searches for the data of the input nucleotide sequence in the nucleotidesequence database. "blastp (Protein Query vs. Protein DB)" searches for the data of the input protein sequence in the protein sequence database. "blastx (DNA Query vs. Protein DB)" searches for the data of the input nucleotide sequence in the protein sequence database by performing six-frame translation of the input nucleotide sequence. "tblastn (Protein Query vs. DNA DB)" searches for the data of the input protein sequence in the nucleotide sequence database by performing six-frame translation of a nucleotide sequence database dynamically. Detailed parameters for BLAST search are set in a details option setting portion 147.

As a "View Route" button 144 is depressed, FIG. 6, which is the overall view of the database network, is displayed, enabling the locations of KeyDB and TargetDB to be confirmed. In a field 148, the search route set in the route table is displayed.

In step 23, as a search start button 145 is depressed, a search begins. Initially, a search program (BLAST) in the homology search portion 123 is activated, and then a homology search is conducted between the inputted sequence data and the homology search data in the database designated as KeyDB in order to acquire the ID of the candidate data. Then, a search program in the ID search portion 122 is activated, and, using as a starting point the ID of KeyDB obtained by the homology search, a search is conducted for a corresponding ID of TargetDB by following the route of the links set in the route table.

Figure 19:
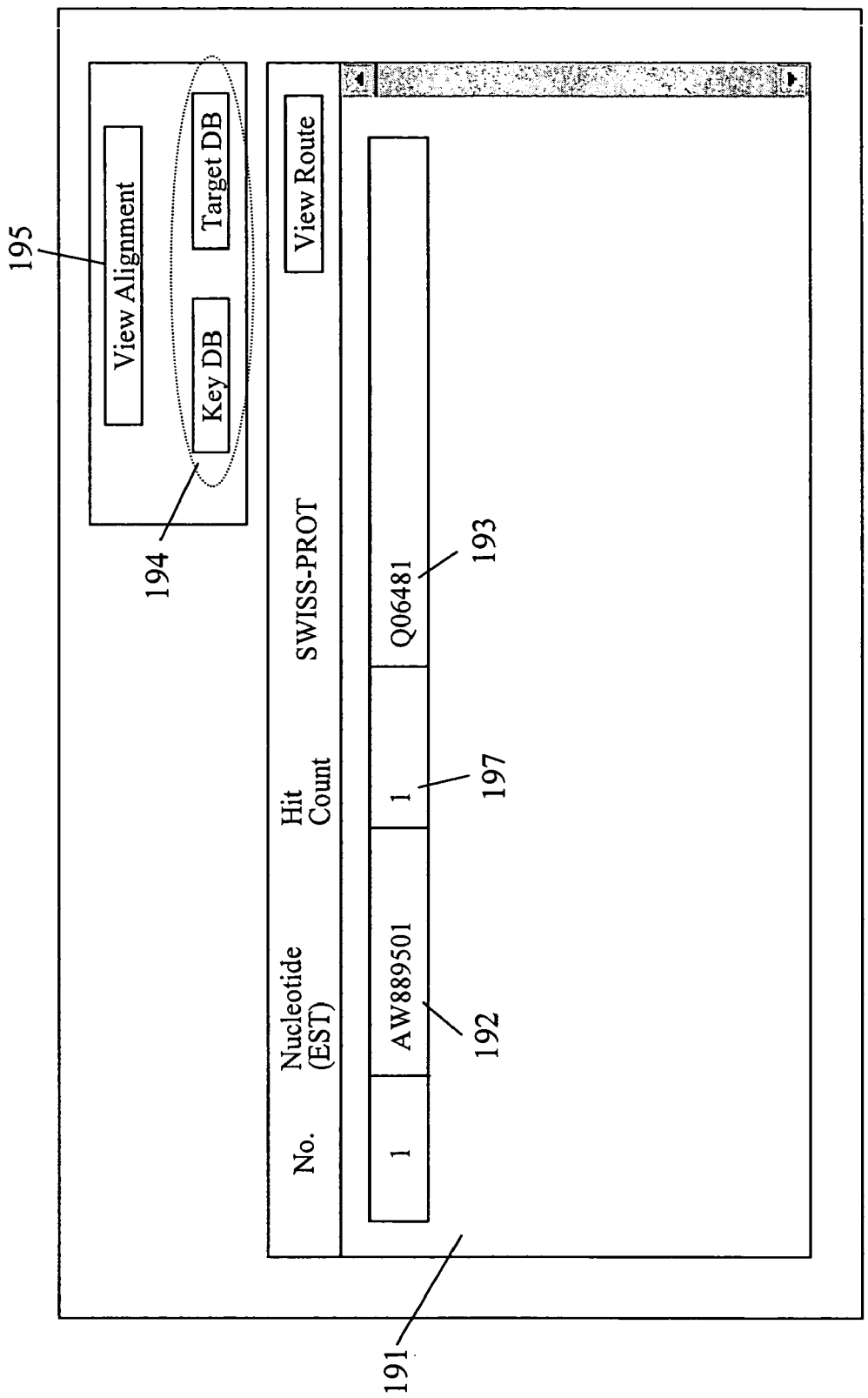
FIG. 19 shows an example of the screen of a display portion on which search result is displayed.
Figure 21:
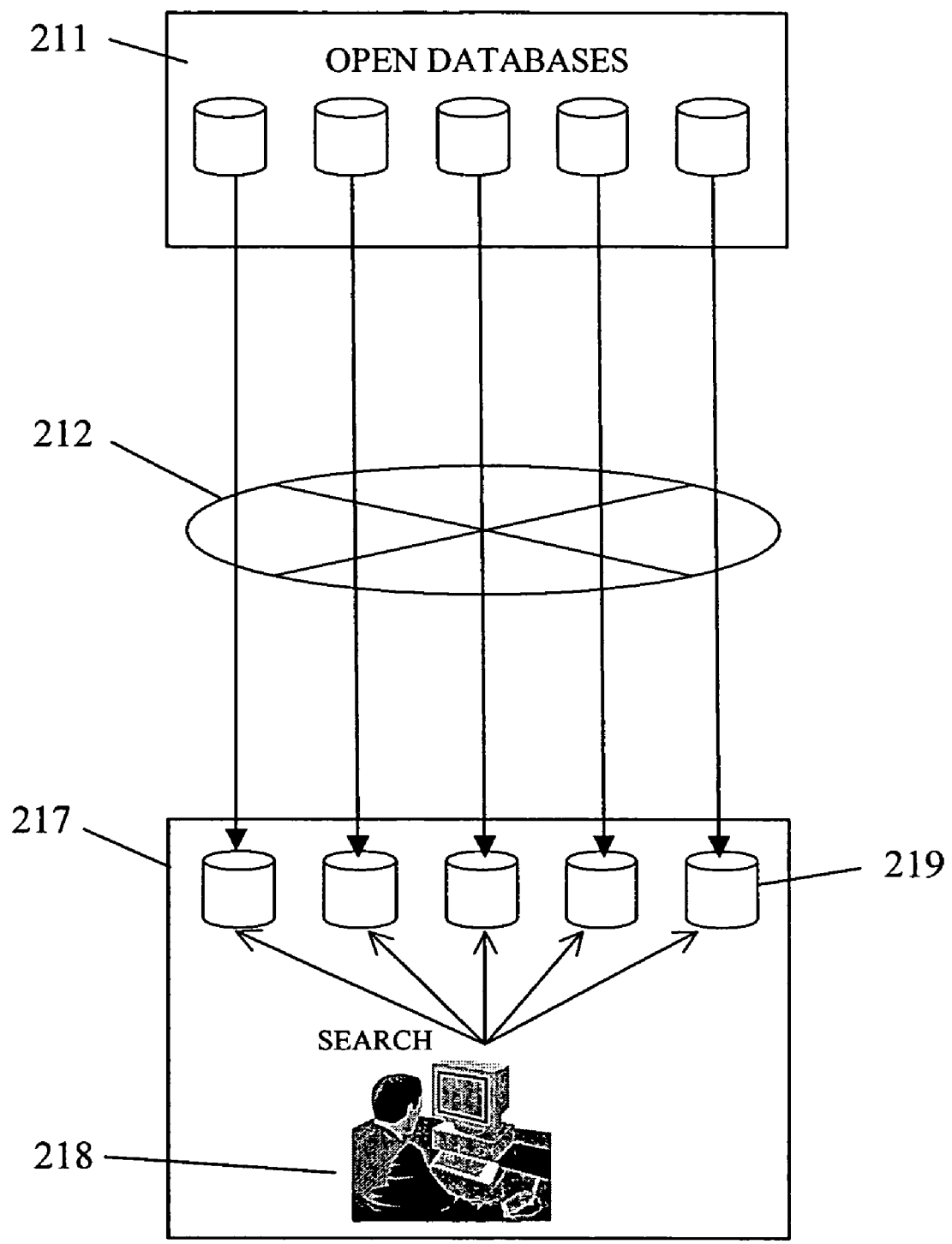
FIG. 21 schematically shows a conventional search system that downloads data from databases on the Web.

In step 24, the search result is displayed. FIG. 19 shows an example of the screen of the display portion on which the search result is displayed. In the illustrated example, an ID 193 of TargetDB (SWISS-PROT) that corresponds to the ID 192 of KeyDB (Nucleotide (EST)) is shown in a field 191. In "Hit Count" 197, the number of IDs in SWISS-PROT, which is TargetDB, that corresponds to the ID of KeyDB, that is Nucleotide (EST), is shown. By clicking a "KeyDB" button or "TargetDB" button 194, a detailed description as shown in FIG. 17 can be displayed. By clicking a "ViewAlignment" button 195, a homology search result as shown in FIG. 20 can be displayed. In FIG. 20, "E-value" refers to an expected value, and "Score" refers to a homology value (Altschul, S. F., Gish, W., Miller, W., Myers, E. W. & Lipman, D. J. (1990) "Basic local alignment search tool." J. Mol. Biol. 215: 403-410). An ID search is conducted using the ID with the highest Score data as a search key.

Thus, in accordance with the invention, all of the databases on a network can be easily searched for data by following links in the network.

What is claimed is:

1. A data search system comprising a data center for gathering data from a plurality of biological information databases and for distributing data and a user's facility for receiving the data distributed from the data center to use the data for a data search, the data center including at least one computer which comprises:

means for downloading data from a plurality of biological information databases;
means for generating link information which shows how the plurality of biological information databases are associated by extracting information on how a data entry in a database associates with another data entry in another database from the downloaded data;
means for generating detailed information by extracting an ID of a data entry and an explanation of the data entry from each data entry, in the downloaded data;
means for generating data for homology search by extracting the ID and sequence data of the data entry from said each data entry, in the downloaded data;
a route table in which information of permitted routes among the biological information databases is stored;
means for distributing to the user's facility the link information, the detailed information of said each data entry, the data for homology search, and the route table, and the user's facility including at least one computer which comprises:
means for conducting the data search using the link information, the detailed information of said each data entry, the data for homology search, and the route table distributed from the data center, wherein the route table stores a data search rule which restricts searches routes for each database of the plurality of biolociical information databases, and wherein the means for conducting the data search in the user's facility conducts the data search by following only the permitted routes which are defined in the route table and among search routes indicated by the link information.

2. A data search method implemented by a data center and a user's facility, comprising:

gathering by a computer in the data center data from a plurality of biological information databases by: downloading data from a plurality of biological information databases; generating link information which shows how the plurality of biological information databases are associated by extracting information on how a data entry in a database associates with another data entry in another database from the downloaded data; generating detailed information by extracting an ID of a data entry and an explanation of the data entry from o-f each data entry in the downloaded data; generating data for homology search by extracting the ID and sequence data of the data entry from each data entry in the downloaded data; and maintaining a route table in which information of permitted routes among the biological information databases is stored;
distributing by the computer in the data center to the user's facility the link information, the detailed information of said each data entry, the data for homology search, and the route table; and
conducting by a computer in the user's facility the data search using the link information, the detailed information of said each data entry, the data for homology search, and the route table distributed from the data center, wherein the route table stores a data search rule which restricts searches routes for each database of the plurality of biological information databases, and wherein the step of conducting the data search in the user's facility is conducted by following only the permitted routes which are defined in the route table and among search routes indicated by the link information.

* * * * *